United States Patent
Zhai et al.

(10) Patent No.: US 10,595,826 B2
(45) Date of Patent: Mar. 24, 2020

(54) HEART RATE ASSISTANCE FOR PHASE DETERMINATION IN ECHOCARDIOGRAPHY

(71) Applicants: Liang Zhai, Castro Valley, CA (US); Wilko Wilkening, Mountain View, CA (US)

(72) Inventors: Liang Zhai, Castro Valley, CA (US); Wilko Wilkening, Mountain View, CA (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 485 days.

(21) Appl. No.: 15/366,286

(22) Filed: Dec. 1, 2016

(65) Prior Publication Data

US 2018/0153514 A1 Jun. 7, 2018

(51) Int. Cl.
*A61B 8/00* (2006.01)
*A61B 8/02* (2006.01)
(Continued)

(52) U.S. Cl.
CPC .......... *A61B 8/463* (2013.01); *A61B 5/0022* (2013.01); *A61B 5/0245* (2013.01); *A61B 5/02427* (2013.01); *A61B 5/02444* (2013.01); *A61B 5/681* (2013.01); *A61B 5/7289* (2013.01); *A61B 5/743* (2013.01); *A61B 8/02* (2013.01); *A61B 8/0883* (2013.01); *A61B 8/486* (2013.01); *A61B 8/488* (2013.01); *A61B 8/5223* (2013.01); *A61B 5/02438* (2013.01); *A61B 8/543* (2013.01)

(58) Field of Classification Search
CPC .............. A61B 5/0022; A61B 5/02427; A61B 5/02438; A61B 5/02444; A61B 5/0245; A61B 5/681; A61B 5/7289; A61B 5/743; A61B 8/02; A61B 8/0883; A61B 8/463; A61B 8/486; A61B 8/488; A61B 8/5223; A61B 8/543
See application file for complete search history.

(56) References Cited

U.S. PATENT DOCUMENTS 6,661,161 B1 * 12/2003 Lanzo ................. A61B 7/00
                                                         310/334
2003/0114759 A1 * 6/2003 Skyba ................. A61B 8/08
                                                         600/458

(Continued)

FOREIGN PATENT DOCUMENTS

| CN | 20152012764 | 7/2015 |
| JP | 2009172186 | 8/2009 |
| JP | 5689927 | 3/2015 |

OTHER PUBLICATIONS

Extended European Search Report (EESR) dated May 7, 2018 in corresponding European Patent Application No. 17203826.7.

*Primary Examiner* — Michael W Kahelin
*Assistant Examiner* — Vynn V Huh (57) ABSTRACT

A heart rate monitor provides a pulse or heartbeat, but without the on-going or continuous phase signal of ECG and/or with a delay relative to the actual heartbeat. For phase determination in echocardiography, the heartbeat from the heart rate monitor is used to assist in identification of phase from acquired ultrasound data. Rather than relying on just ECG or just image processing, the worn or handheld heart rate monitor is used to simplify the image process-based identification of phase.

14 Claims, 4 Drawing Sheets

(51) Int. Cl.
  *A61B 5/00*   (2006.01)
  *A61B 8/08*   (2006.01)
  *A61B 5/0245*   (2006.01)
  *A61B 5/024*   (2006.01)

(56) References Cited

U.S. PATENT DOCUMENTS

| | | | |
|---|---|---|---|
| 2004/0059224 A1* | 3/2004 | Varghese | A61B 8/08 |
| | | | 600/450 |
| 2005/0033179 A1* | 2/2005 | Gardner | A61B 8/0883 |
| | | | 600/458 |
| 2005/0113703 A1* | 5/2005 | Farringdon | A61B 5/0428 |
| | | | 600/509 |
| 2009/0214090 A1 | 8/2009 | Hayes | |
| 2012/0078083 A1 | 3/2012 | McConnell et al. | |
| 2014/0128735 A1* | 5/2014 | Newell | A61B 8/543 |
| | | | 600/440 |
| 2015/0094592 A1 | 4/2015 | Ravindran et al. | |
| 2015/0297134 A1* | 10/2015 | Albert | A61B 5/681 |
| | | | 600/384 |

* cited by examiner

HEART RATE ASSISTANCE FOR PHASE DETERMINATION IN ECHOCARDIOGRAPHY

BACKGROUND

The present embodiments relate to the use of physiological cycle information in medical imaging. In particular, phase of the heart cycle is detected for use in echocardiography imaging. Knowing the phase for acquired images allows for reviewing and comparing ultrasound images or clips recorded at different cycles but a same phase of the heart cycle.

Electrocardiography (ECG or EKG) records the electrical activity of the heart with electrodes placed on the skin. These electrodes detect the small electrical changes on the skin that arise from the heart muscle's electrophysiological pattern during each heartbeat. During the examination, multiple electrodes are attached to the patient's chest, arms or legs with adhesive patches. Body hair and perspiration may make the electrical contact unreliable. The adhesive patches may also cause discomfort to the patient. Cables are then connected to the patches and the ultrasound system. Applying, connecting, disconnecting and removing the electrodes and cables costs time. Obtaining ECG may be cumbersome in circumstances such as stress echo, high patient volumes, tight exam space, or emergencies.

To avoid electrode patches and cables, the ultrasound images may be processed to identify the phases for different images. Depending on the type or mode of ultrasound imaging, this image processing may be inexact, incapable of real-time identification of phase, and/or overly complex.

BRIEF SUMMARY

By way of introduction, the preferred embodiments described below include methods and systems for phase determination in echocardiography. A heart rate monitor provides a pulse or heartbeat, but without the on-going or continuous phase signal of ECG and/or with a delay relative to the actual heartbeat. The heartbeat from the heart rate monitor is used to assist in identification of phase from acquired ultrasound data. Rather than relying on just ECG or just image processing, the worn or handheld heart rate monitor is used to simplify the image process-based identification of phase.

In a first aspect, an ultrasound system is provided for phase determination in echocardiography. A wireless heart rate sensor is for providing a pulse signal for a patient. The pulse signal indicates one heart beat without phasing per cardiac cycle. An ultrasound echocardiography scanner is configured to wirelessly receive the pulse signal, acquire an ultrasound image from a scan of the patient, and determine a phase for the ultrasound image with the pulse signal. A display is configured to display the ultrasound image and the phase.

In a second aspect, a method is provided for phase determination with an echocardiographic ultrasound system. A heart rate is received from a heart rate monitor. Ultrasound data of the echocardiographic ultrasound system is image processed, identifying a part of a heart cycle for the ultrasound data using the heart rate. An image is generated from the ultrasound data and the part of the heart cycle.

In a third aspect, a method is provided for phase determination with an echocardiographic ultrasound system. The echocardiographic ultrasound system acquires a sequence of images of a patient. A heartbeat of the patient is detected. The heartbeat is an instantaneous signal that is periodic with repetition of a heart cycle of the patient. The sequence is aligned with the heart cycle using the heartbeat. The sequence of the images is displayed based on the aligning.

The present invention is defined by the following claims, and nothing in this section should be taken as a limitation on those claims. Further aspects and advantages of the invention are discussed below in conjunction with the preferred embodiments and may be later claimed in combination or independently. Various features and advantages discussed herein may or may not be provided by different embodiments of the invention.

BRIEF DESCRIPTION OF THE DRAWINGS

The components and the figures are not necessarily to scale, emphasis instead being placed upon illustrating the principles of the invention. Moreover, in the figures, like reference numerals designate corresponding parts throughout the different views.

DETAILED DESCRIPTION OF THE DRAWINGS AND PRESENTLY PREFERRED EMBODIMENTS

Currently, ultrasound systems rely on ECG modules with multiple wired electrodes. The ECG module is replaced by a wireless ECG or heartbeat monitor, which is used for heart cycle alignment. Unlike ECG, wireless heart rate monitoring devices are significantly smaller. No electrode patches need to be adhered to the patient's body. For echocardiography, using the wireless heartbeat monitor eliminates cables and the need to place multiple electrodes on the patient. Examination time is reduced, resources (e.g., disposable patches) are saved, and the monitor is more comfortable for the patient.

The combination of a wireless heart rate sensor and signal and/or image processing of ultrasound data may achieve reliable detection of the heart cycle (e.g., duration and/or phase). Based on the phase identification, cardiac parameters may be calculated, and cardiac images and videos may be aligned. Ultrasound images such as M, color, or Doppler modes, may be used to calibrate and/or align the cardiac phase and heartbeat measured by sensor. Relative cardiac phase between recorded heartbeats may be used to temporally align images acquired at different times.

Figure 1:
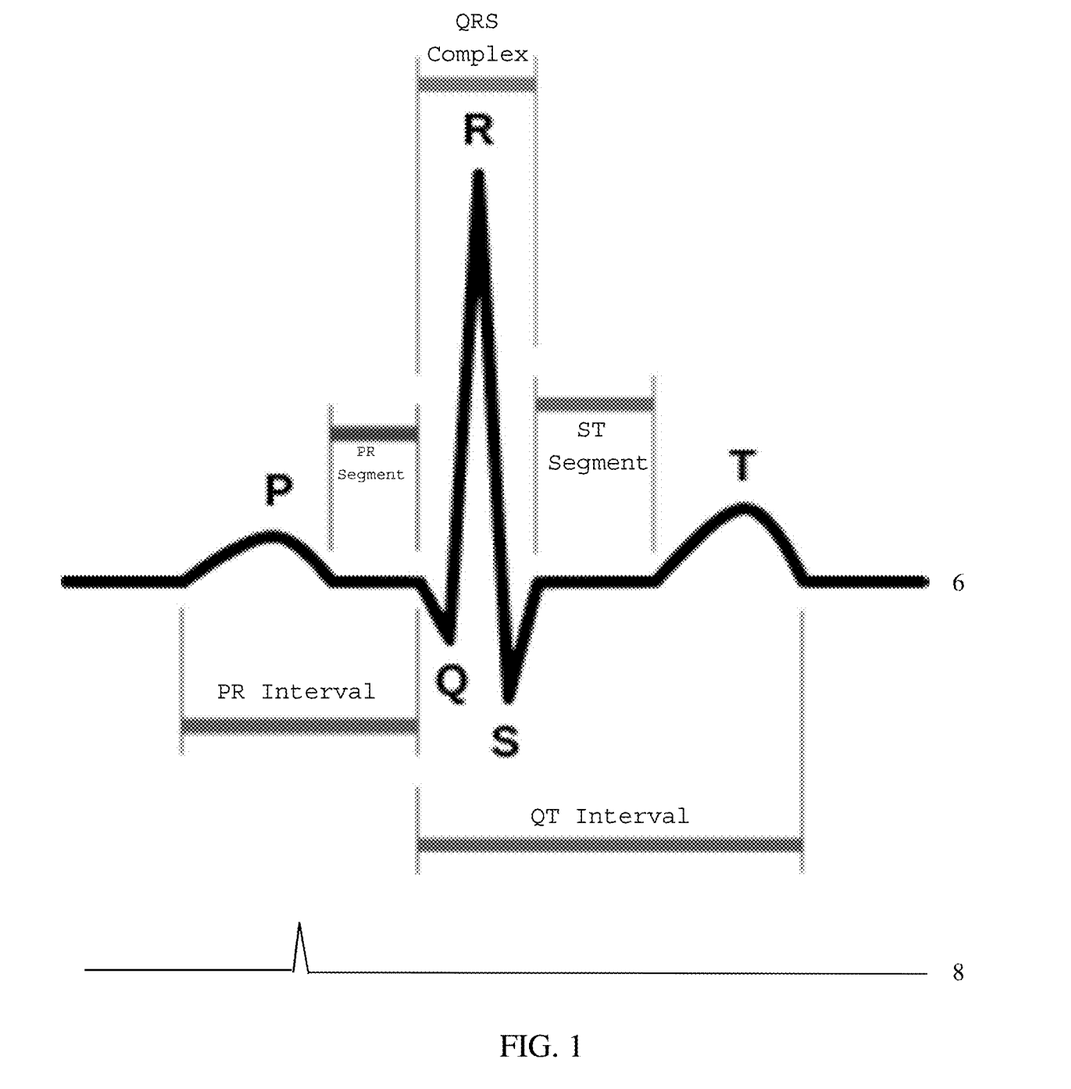
FIG. 1 illustrates an example ECG signal showing phase information throughout a heart cycle and an example heartbeat signal.

FIG. 1 shows a heart cycle waveform 6. The heart cycle waveform 6 includes various labeled phases, such as the PQRST phases. Different intervals or segments of the heart cycle are shown. The heart cycle waveform may be produced by an ECG device measuring electrical activity of the heart. Different parts or phases of the heart cycle are represented for each repetition of the cycle. Conversely, a pulse or heart rate signal 8 may provide a beat or instantaneous measure once or twice per heart cycle. The waveform for other parts of a given heart cycle may not be provided.

For example, a heart rate signal 8 may provide a frequency or rate for the heart as a pulse occurring once a cycle or as a numerical value (e.g., 1.1 seconds) rather than a continuously varying waveform.

The heart rate or pulse signal may be delayed relative to the actual heart cycle. For example, optically or mechanically sensing a pulse on a wrist or leg results in a mechanical delay. The pulse wave mechanically travels through the circulatory system to reach the wrist or leg, so is delayed relative to the heart. Similar delays may occur even for simple electrode-based heart rate monitors, such as due to communications and/or processing delay. ECG devices, with the many electrodes and cables, are designed to avoid such delays and provide the signal representing activity throughout the entirety of each cycle. Image processing is used to make up for the lack of ECG waveform while the pulse signal simplifies the image processing.

Figure 2:
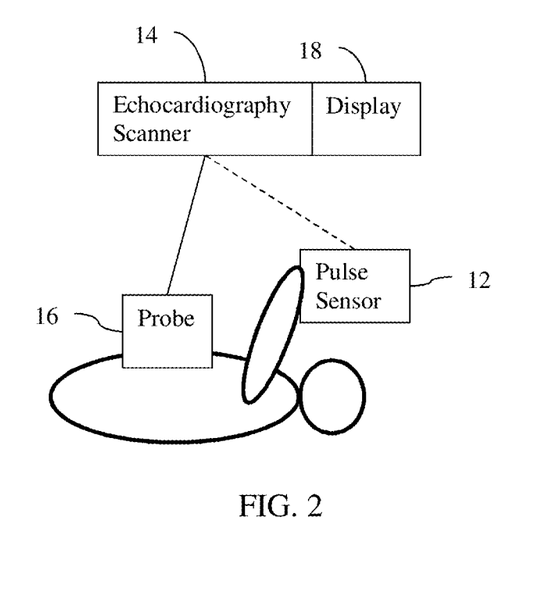
FIG. 2 is a block diagram of one embodiment of an ultrasound system for phase determination in echocardiography.

FIG. 2 shows one embodiment of an ultrasound system for phase determination in echocardiography. A heart rate monitor or pulse sensor 12 is used to identify a phase at which ultrasound data is acquired by the echocardiography scanner 14. The signal from the pulse sensor 12 is not a replacement for ECG, but is instead used to assist in processing the ultrasound data to determine the phase for the ultrasound data. This assistance may limit the amount of processing, increase the rate of identification, and/or be used to simulate an aligned heart cycle signal.

The ultrasound system includes the pulse sensor 12 and the echocardiography scanner 14 with a corresponding probe 16 and display 18. Additional, different, or fewer components may be provided. For example, a network for communication with a computer, server, workstation, or other processor is provided. As another example, the pulse sensor 12 is integrated with the echocardiography scanner 14, such as being on a handle connected to the housing of the scanner 14.

The pulse sensor 12 is a heart rate sensor. The pulse sensor 12 is a camera, a light emitting diode, a strain gauge, an electrode, set of only two electrodes, microphone, processor, analog-to-digital converter, filters, amplifier, combinations thereof or other now known or later developed sensor for sensing a pulse or heartbeat. For example, the sensor 16 is an optical sensor for sensing blood flow at or near the skin surface. Infrared or other pulse sensor may be used. As another example, the pulse sensor 12 is a mechanical sensor, such as a strain gauge, for sensing flexing in the patient caused by the heartbeat. In other embodiments, the pulse sensor 12 is one or two electrodes for sensing electrical activity of the heart. The electrodes are handheld or rest against the skin without adhesive. Due to the lack of attachment and few number of electrodes, a less accurate or incomplete representation of the waveform throughout the heart cycle is provided.

The pulse sensor 12 is handheld or wearable. For example, the pulse sensor 12 includes a housing to be held by one or two hands of a patient during use. As another example, the pulse sensor 12 is in or on a wrist band, arm band, leg band, or ankle band. In other examples, the pulse sensor 12 is on a necklace. The pulse sensor 12 is positioned against the skin of the patient and held in place by a band, pressure, gravity, the patient, or the sonographer. Adhesive electrode patches or another adhesive are not used. Gel may be used to assist in conductivity. In other embodiments, the pulse sensor 12 is adhered to the patient's body.

During use, the pulse sensor 12 provides a pulse signal for the patient. The pulse signal indicates one heart beat without phasing per cardiac cycle. A beat occurring at only one part in each of the cardiac cycles is detected without information for other parts of each of the cardiac cycles. Depending on the technology used, such devices only detect the pulse and cannot provide accurate information about the phase of the heart cycle or such devices may come close to the performance of a traditional ECG system but without the accuracy. Instead of seven or other number of lead ECG, a simple and cheap heart rate monitoring device is used. While the conventional ECG solution provides the heart rate and the exact phase within the heart cycle with respect to a known time reference (e.g., the absolute time of the R-wave), the pulse sensor 12 does not provide accurate information about the phase, or the phase information is not available at all.

The pulse sensor 12 includes a transmitter or transceiver for wireless communication. Using Bluetooth, Wi-Fi, direct radio link, broadcast, or other communications format, the pulse sensor 12 outputs the heartbeat or heart rate signal wirelessly. By using wireless communications, cables may be avoided. In alternative embodiments, wired communication is used with just one cable or wire. Instead of multiple wires from different electrodes, one wire is used to communicate the pulse.

The ultrasound echocardiography scanner 14 is a medical diagnostic ultrasound system. A general ultrasound system or a cardiac specific ultrasound system may be used. The scanner 14 is a cart-based, handheld, portable, or other ultrasound system operable to scan a patient with acoustic energy. The scanner 14 is configured by hardware, software, and/or firmware to scan the patient, acquiring ultrasound data. The ultrasound data is image data representing the patient at a given time. An on-going acquisition may be used to acquire ultrasound data or images representing the patient over time or through a sequence.

The scanner 14 includes the probe 16, a beamformer, an image processor, and the display 18. Additional, different or fewer components may be provided. The beamformer is operable to ultrasonically scan a region with transmission and reception from the probe 16. In response to the received echo signals, a frame of ultrasound data representing the patient at a given time or period is formed. The image processor detects and generates an image of the scanned region using the frame of data. One or more modes of detection and corresponding image processors may be used, such as B-mode, M-mode, color, flow, Doppler, spectral Doppler (e.g., pulsed wave Doppler or continuous wave Doppler), or others. For example, B-mode, M-mode, color Doppler, or spectral Doppler images are acquired. The generated image or images are then provided on the display 18.

Heart cycle information may also be output to the display 18. The heart cycle information may be a simulated ECG waveform, heart rate, or pulse. Alternatively or additionally, the displayed images may be responsive to the detected heart phase. A sequence of images may be repeated where the beginning and/or ending images of the sequence are selected based on the heart phase (e.g., end diastole due to relative relaxed state of the heart). Detected events associated with a physiological cycle may also be indicated.

To detect the phase for any frame of ultrasound data or image, the scanner 14 receives the pulse signal from the pulse sensor 12. A receiver or interface receives the pulse signal. The signal is received wirelessly, but wired connection may be used. The pulse signal may be delayed or offset in time relative to actual pulsing by the heart.

In one embodiment, the echocardiography scanner 14 and the pulse sensor 12 have the same reference time, such as sharing a clock signal or oscillator. Heartbeat data is measured and recorded continuously and stored within the pulse sensor 12 and/or scanner 14 with time stamps. The scanner 14 also records the time stamp for all saved images or ultrasound data. The heartrate data and image data are merged together based on the time stamps. The occurrence of the pulse relative to the occurrence of an image is known from the time stamps. The images and pulse signals may be merged in an ongoing manner or from time to time (e.g., after the examination or every a few minutes).

In another embodiment, the pulse sensor 12 and the scanner 14 do not have a shared clock, so synchronization is used. For example, the scanner 14 adds a time stamp upon receipt of each pulse or update from the pulse sensor 12. The relative time stamps from the pulse sensor 12 and the scanner 14 are used to synchronize. In other approaches, communications between the pulse sensor 12 and the scanner 14 are used to synchronize together. The pulse sensor 12 transmits data to the scanner 14 frequently and is constantly synchronized with the imaging system when or as ultrasound images are acquired.

The scanner 14, using the image processor, a control processor, or another processor, computes the cardiac phase for one, some, or each acquired ultrasound image. The phase is determined, in part, with the pulse signal. Since the pulse signal from the pulse sensor 12 may not include the full or accurate heart cycle waveform 6, the phase for a given ultrasound image may not be determined using just the pulse signal or heart rate. The scanner 14 applies image processing to determine the phase for a given ultrasound image or data set. The image processing is assisted by the pulse signal.

Figure 3:
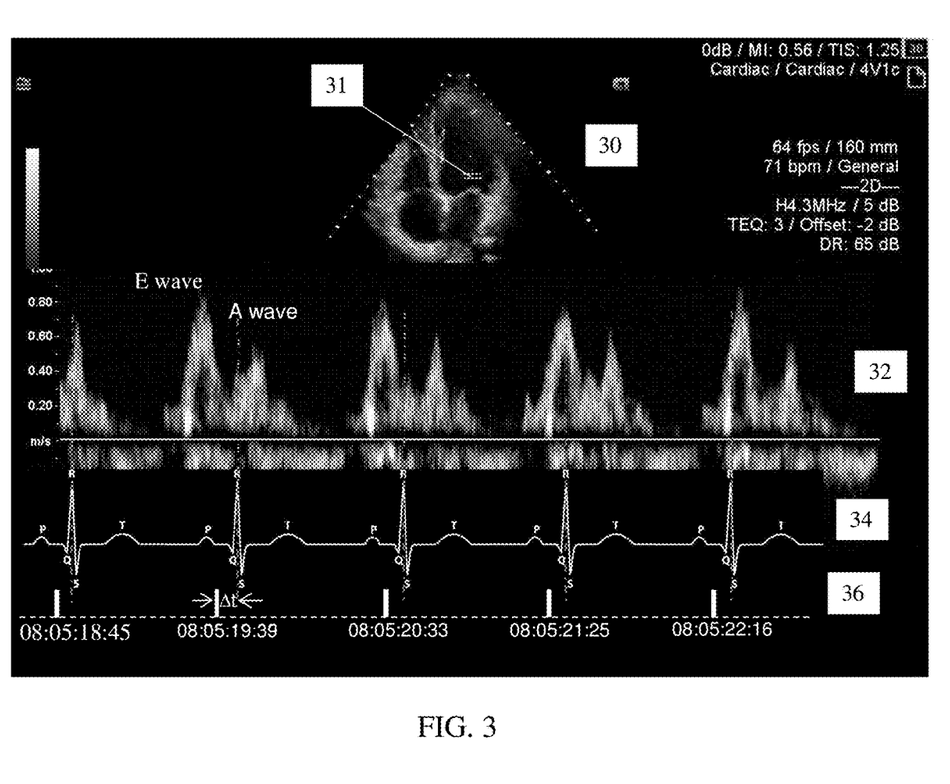
FIG. 3 is an example B-mode and PW mode ultrasound image with a heartbeat signal and a fit heart cycle or simulated ECG.

FIG. 3 shows an example context for identifying phase using image processing and the pulse signal 36. A B-mode image 30 of a left ventricle of a patient is continuously updated. A range gate 31 is positioned in the B-mode image. A pulsed wave Doppler (PW Doppler) image or trace 32 is generated as an ongoing scroll where each vertical line represents the spectral content at the range gate location for a given time. The pulse sensor 12 supplies the pulse signal 36. The time stamps for each beat or pulse are shown. The heart cycle waveform 34 is simulated or shown for discussion purposes. The goal is to identify the phase of the heart cycle at any given time even though the pulse signal 36 does not occur at a specific phase. The heart cycle waveform 34 may provide the phase at each time, but is not available from an ECG device.

The PW strip or trace 32 is used to calibrate the phase of the simulated the ECG waveform 34. The A waves are identified in the PW data and used to position the simulated R wave in the heart cycle waveform 34. The A-wave in PW Doppler corresponds to the R-wave in an ECG or heart cycle waveform 34. The time delay between the recorded time stamps and A waves (i.e., cardiac event or phase) are computed as Δt. Δt may be computed for each heart cycle and/or averaged from multiple cardiac cycles. Δt is used to align the cardiac phase with the recorded time stamps or in other ways to identify the phase.

In alternative embodiments, the pulse signal 36 is used without determining Δt. The time stamp or beat signal is used in other ways, such as limiting a search to be within a temporal range or spatial location.

The pulse signal, time stamp, Δt, or other information from the pulse signal is used with image processing of the ultrasound image to identify the phase at a given time or for a given image. The identification is repeated for each image in a sequence. Alternatively, the identification of the same phase in different cycles is used to determine phases throughout those cycles. In other embodiments, the identification of the same phase or one phase is used with a different image process to identify other phases, such as by tracking motion of the heart.

Any image processing may be used with any modality of ultrasound imaging. A machine-learnt classifier may indicate a phase and/or determine whether a given image represents a particular phase. Spectral analysis, automatic tracing (e.g., amplitude thresholding in spectral Doppler), fitting a model labeled by phase for particular deformations, or other image processing-based approach may be used to identify the phase. Which phase is represented by an image is identified. Alternatively, whether the image represents a given phase is identified.

In one embodiment, the pulse signal assists in image processing by spatially limiting the image processing. While it is possible to determine heart rate and phase from image data without knowing the approximate heart rate, such approaches are computationally costly and less robust as other methods (e.g. finding shapes in images) have to be used to first identify structures that can then be used to detect the heart rate and phase. The pulse signal may be used for identifying the locations of structure, which is then used to find phase without interference by other structure. The pulse signal may be used to limit the image processing spatially.

Structure (e.g., anatomy, flow, or combinations thereof) that varies with the heart cycle is identified from the ultrasound data. Ultrasound images may show parts of the heart as well as other tissue and organs. Some parts of the image, such as the ventricle wall and the mitral valve, move at the frequency of the heart cycles. The structure exhibits cyclic changes at the same frequency as the heart rate. The heart rate from the pulse sensor 12 is used to establish the frequency. Alternatively, a default heart rate is used. By dividing the image into small segments (e.g., kernels or patches) and computing the Fourier transform of the mean brightness of every segment, segments that show motion that correlates with the heart rate or an integer multiple thereof are identified. The segments with a primary frequency within a tolerance threshold of the heart rate are identified.

Other methods can be used for the identification of the structure. For example, motion vectors between consecutive images may be calculated. The direction of the motion or the magnitude of the motion may be identified as being associated with the heart rate. The locations in the image corresponding to the heart are found, in part, using the heart rate from the pulse sensor 12.

Image and signal processing algorithms are then employed to detect the phase of the heart cycle. For example, by identifying opening and closing action of the mitral valve or by determining the maximum contraction of the left ventricle, the phase is determined. A fit model or other approach is used to determine the phase represented by the identified segments for the image. As another example represented in FIG. 3, the maximum amplitude over time in the PW Doppler trace 32 is tracked and the amplitude corresponding to the A-wave is found based on variation characteristics. Besides PW mode, any motion images and/or signals such as color Doppler imaging, color Doppler M mode, elastography, and continuous wave Doppler may be used for calibration.

Alternatively or additionally, the pulse signal is used to temporally limit the search. Where the image processing identifies whether an ultrasound image represents a particular phase, the pulse signal may be used to limit the number of images searched. For example, Δt may be used to identify a range (e.g., pulse+Δt+/−period) of images to process and another range of images not to process.

In another embodiment, a heart cycle trace or waveform 34 is fit to the pulse signal 36. Image processing is used to identify a cardiac event, such as the A-wave. By calculating Δt, the occurrence of this same cardiac event relative to each occurrence of the pulse in the pulse signal 36 is found. The waveform 34 is temporally aligned by scaling each heart cycle to the occurrence of the pulse plus Δt. Once the waveform 34 for a given cycle is fit to two pulses of the pulse signal 36, the ultrasound data associated with any times between the cardiac events are determined based on the scaled waveform 34. The ECG trace (e.g., waveform 34) or an R-wave trigger event is simulated by fitting a typical ECG waveform into the recorded cardiac rate 36. This waveform 34 may be displayed on the screen during the examination or image review.

The relative phase for each ultrasound image or time may be identified. Rather than fitting based on two pulses for each cycle, the cycle beginning time and a cardiac period (e.g., averaged heart rate) are used. The cycle beginning time and/or the cardiac period are based on the pulse signal. The percentage of the cardiac cycle is computed by:

$$\alpha = \frac{t - t_i}{T} \times 100\%$$

α is the percentage of the cardiac cycle at time t (i.e., the time of the particular ultrasound image); $t_i$ is the last heart beat time (i.e., beginning of the heart cycle, such as a pulse time stamp plus Δt); and T is the cardiac period (e.g., period for a given cycle or average of multiple cycles). The relative phase is the percentage of completion of the cardiac cycle, so may be displayed as a number or graph with an ultrasound image.

Other uses of the pulse signal may be used to assist in image processing-based identification of the phase. Images representing the patient at the same phase of different heart cycles are found. Alternatively or additionally, the phase of each ultrasound image is found.

Actual heart rate and phase may be calculated continuously or retrospectively. Under certain conditions, for example in patients with arrhythmia, the correct identification of heart cycles is achieved retrospectively with or without the use of the data from the heart rate monitoring device. For example, if the heart rate monitoring device provides a signal for every detected pulse, heart cycles with irregular length may be identified by correlating the pulse data with image data. If the pulse sensor 12 only provides a heart rate that is computed as an average over multiple detected pulses, more complex algorithms are employed. For example, the ultrasound system establishes a predicted heart rate base on a series of regular beats. A deviation between the predicted heart rate and the heart rate received from the pulse sensor 12 indicates an irregular beat or an error in the detection. Based on subsequent regular beats and additional signal or image processing, irregular beats are identified correctly after their occurrence.

The display 18 is a monitor, LCD, plasma, LED, projector, printer, or other output device for visually representing information. The display 18 is configured by loading display values into a memory or graphics plane. The display 18 is configured to display one or more ultrasound images. Phase information may be displayed with each ultrasound image or some of the ultrasound images. For example, the simulated heart cycle waveform 34 and a marker on the waveform corresponding to the current displayed image is output. As another example, a relative or specific phase is output as a value or alphanumeric text with or on an ultrasound image. In other embodiments, the identified phase is instead or additionally used to create a repeating sequence of images over one or other integer number of cycles. Using the phase, the end of the sequence matches to the phase immediately prior to the beginning of the sequence so the looping or repetition appears more seamless. The heart rate calculated from phases and/or from the pulse sensor 12 may also be displayed, such as displaying the pulses 36 or alphanumeric text for the heart rate.

The echocardiography scanner 14 and/or pulse sensor 12 may include a memory for storing ultrasound data, phase, and/or pulse signal. The memory is a single memory or a plurality of different memories. Any of various now known or later developed memories may be used, such as RAM, removable media, compact disk, magnetic tape, diskette, ROM, cache, buffer or hard drive. Alternatively or additionally, the memory is a computer readable storage medium for storing instructions for a processor. The processor, programmed with the instructions, executes the method of FIG. 4 and/or performs the actions discussed above for the pulse sensor 12 and/or the echocardiography scanner 14.

The echocardiography scanner 14 and/or pulse sensor 12 may include a processor. The processor is a single or multiple processors. The processor is an application-specific integrated circuit, general processor, control processor, digital signal processor, field programmable gate array, digital circuit, analog circuit, combinations thereof, or other now known or later developed device for determining heart rate, generating a pulse signal, identifying phase, generating ultrasound images, using the phase for images, or combinations thereof.

Figure 4:
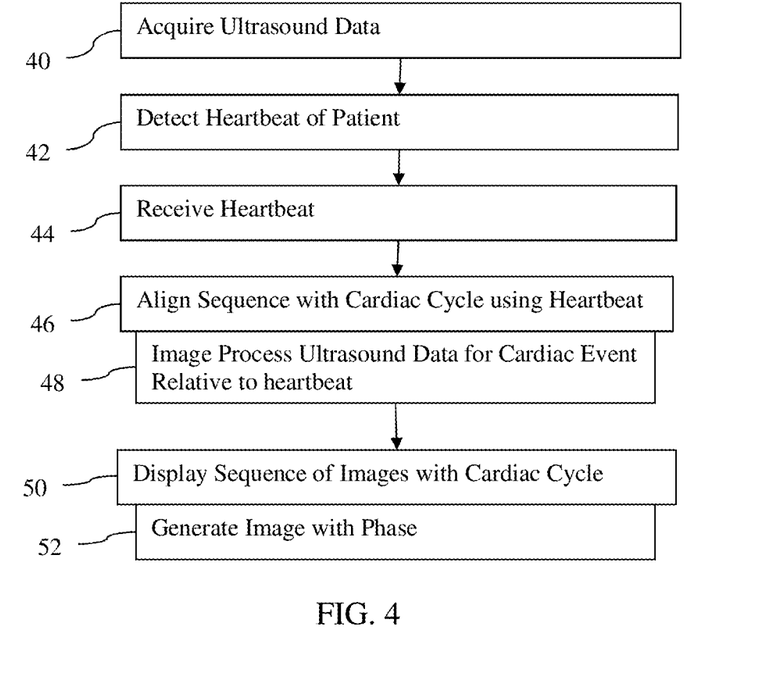
FIG. 4 is a flow chart diagram of one embodiment of a method for phase determination in echocardiography.

FIG. 4 shows one embodiment of a flow chart of a method for phase determination with an echocardiographic ultrasound system. A heart rate monitor is used to assist in temporally aligning an imaging sequence with the cardiac cycle. A heartbeat, such as a pulse, is used to assist image processing to identify phases for images.

The method is implemented by the system of FIG. 2 or another system. An ultrasound system performs acts 40 and 44-52. The heart rate monitor performs act 42. In other embodiments, different devices are used.

The acts are performed in the order shown (top to bottom or numerically) or other orders. In an example of a different order, act 40 is performed simultaneously or after act 42 and/or 44.

Additional, different, or fewer acts may be used. For example, acts 48 and 52 or acts 46 and 50 are not performed. As another example, acts for configuring the ultrasound system to perform an echocardiography scan are provided. In yet another example, acts 50 and 52 are not performed. Act 44 may be performed by an ultrasound system without performance of act 42.

In act 40, ultrasound data is acquired. The ultrasound system, using a transducer probe, transmits acoustic energy and receives reflections or echo signals. Using beamformation, a one, two, or three-dimensional region of the patient is scanned. One complete scan of the region provides a set or frame of ultrasound data. This ultrasound data is image data in that the ultrasound data may be processed to create an image. By repeating the scanning of the region, a sequence of sets or frames of ultrasound data are acquired. Each set or frame represents the region of the patient at different times or periods. Each set or frame corresponds to a phase of the heart cycle, but the specific phase may not be known.

The scanning is configured for echocardiography. The mode or modes of detection and corresponding scan are set for imaging a heart or circulatory system of the patient. For example, B-mode and flow mode in combination with or without spectral Doppler (e.g., PW Doppler) are used.

In act 42, a heart monitor detects a heartbeat of the patient. Using optical, mechanical, electrical, or other physics, the pulse of the patient is detected. An instantaneous signal that is periodic with repetition of a heart cycle of the patient is measured. For example, an optical sensor worn by the patient on their wrist detects the pulse of the patient. The pulse repeats once or twice every heart cycle, so may be communicated as a beat, frequency, or heart rate. Each pulse is detected, and an average and/or each pulse is output.

In act 44, the ultrasound system receives the heart rate from the heart rate monitor. The occurrence of a pulse, an average heart rate, a frequency, or other representation of the detected pulse of the patient is received. The signal is analog or digital, but is just the pulse rather than the waveform representing phases through the entire heart cycle. Alternatively, the waveform representing different phases through the entire heart cycle is received. The receipt is by a wireless receiver, but a wired interface may be used.

In act 46, the sequence of sets or frames of ultrasound data are aligned using the heartbeat. The heartbeat is used to spatially and/or temporally limit the determining of phase used for the alignment. The alignment is in time so that the phase or part of the heart cycle associated with one or more particular sets or frames is determined. For example, a cardiac event is detected in one or the images of the sequence. A delay of the heartbeat relative to the cardiac event is determined in order to correlate or align the timing of the sequence with the heart cycle.

Act 48 represents one approach to use of the heartbeat for aligning. The ultrasound system image processes the ultrasound data. The image processing identifies a part (e.g., phase) of the heart cycle represented by the ultrasound data. The heartbeat or heart rate is used for this image processing. For example, the heart rate is used to identify spatial locations or segments associated with heart cycle motion. This spatial limit avoids processing other segments or locations, instead focusing the phase detection on the heart related motion. As another example, the search is temporally limited. The heartbeat indicates occurrence of the heart cycle. By limiting the search in the ultrasound data for a particular phase to a temporal range established by or relative to the heartbeat, the number of ultrasound images processed for a given phase is limited. The delay, positive or negative, of the heartbeat relative to a cardiac event detected from one frame of ultrasound data may be used to limit the search for that same phase in other cycles or other phases in the same or other cycles.

Once the phase is determined and/or the sequence is aligned with the heart cycle, the phase information may be used to calculate heart-related parameters. Variation in heart rate may be found. Variation in volume or flow may be determined. Images of the heart at different cycles but a same phase may be compared. Differences in volume, motion, or other characteristic between cycles may be calculated. Images of the heart at different phases of a same cycle may be compared. Differences in volume, motion, or another characteristic in a cycle may be compared.

In one embodiment, the sequence is clipped to begin and end at a same or adjacent phases. The clip includes images representing the heart through one or other integer number of heart cycles. Individual images may be selected for static display in other embodiments.

In act 50, the ultrasound echocardiography system displays the sequence of ultrasound images. The sequence is based on the alignment. The beginning and ending phase are selected. Alternatively, a phase of each ultrasound image through the sequence is shown. In other embodiments, an image with or without indication of the phase is displayed. The user may select a phase or time point along a simulated ECG trace, and the ultrasound image representing that phase is displayed.

In act 52, one or more images are generated from the ultrasound data. The images are for any mode of imaging, such as B-mode, color, flow, spectral Doppler, and/or M-mode. The image is one in a sequence or is an image extracted from a sequence.

The image is generated based on the alignment or part of the heart cycle identified in act 48. By knowing the part of the heart cycle, the image associated with a user or automatically selected part of the heart cycle (e.g., end systole) may be displayed. The identification of occurrence of the same part of the cycle in different cycles allows display of corresponding images for comparison. Images from different parts of the same or different cycles may be displayed for comparison.

While the invention has been described above by reference to various embodiments, it should be understood that many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

We claim:

1. An ultrasound system for phase determination in echocardiography, the system comprising:
   a wireless heart rate sensor for providing a pulse signal for a patient, the pulse signal indicating one heart beat without phasing per cardiac cycle;
   an ultrasound echocardiography scanner configured to wirelessly receive the pulse signal, acquire an ultrasound image from a scan of the patient, and determine a phase for the ultrasound image to align with the pulse signal, the ultrasound echocardiography scanner configured to determine the phase for the ultrasound image with a delay between the pulse signal and a cardiac event; and
   a display configured to display the ultrasound image and the phase.

2. The ultrasound system of claim 1 wherein the wireless heart rate sensor comprises an optical or mechanical pulse sensor.

3. The ultrasound system of claim 1 wherein the wireless heart rate sensor comprises only one or two electrodes of a handheld or wrist sensor.

4. The ultrasound system of claim 1 wherein the wireless heart rate sensor comprises a handheld or wearable sensor without any cable and without any adhesive electrode patch.

5. The ultrasound system of claim 1 wherein the pulse signal comprises a beat occurring at only one part in each of the cardiac cycles without information for other parts of each of the cardiac cycles.

6. The ultrasound system of claim 1 wherein the ultrasound echocardiography scanner is configured to acquire the ultrasound image as a B-mode, M-mode, color Doppler, or spectral Doppler image.

7. The ultrasound system of claim 1 wherein the ultrasound echocardiography scanner is configured to determine the phase for the ultrasound image from the ultrasound image and with the pulse signal.

8. The ultrasound system of claim 1 wherein the ultrasound echocardiography scanner is configured to determine the phase for the ultrasound image with image processing of a sequence of images including the ultrasound image, the image processing having a search temporally limited by the pulse signal.

9. The ultrasound system of claim 1 wherein the ultrasound echocardiography scanner is configured to determine the phase for the ultrasound image from a heart cycle trace fit to the pulse signal.

10. The ultrasound system of claim 1 wherein the ultrasound echocardiography scanner is configured to determine the phase for the ultrasound image as a relative phase at a time of the ultrasound image based on a cycle beginning time and a cardiac period, the cycle beginning time and/or the cardiac period being a function of the pulse signal.

11. The ultrasound system of claim 1 wherein the display is configured to display the phase as a percentage of the cardiac cycle or a marking on a simulated electrocardiography trace.

12. An ultrasound system for phase determination in echocardiography, the system comprising:
a wireless heart rate sensor for providing a pulse signal for a patient, the pulse signal indicating one heart beat without phasing per cardiac cycle, wherein the wireless heart rate sensor comprises an optical or mechanical pulse sensor;
an ultrasound echocardiography scanner configured to wirelessly receive the pulse signal, acquire an ultrasound image from a scan of the patient, and determine a phase for the ultrasound image to align with the pulse signal; and
a display configured to display the ultrasound image and the phase.

13. An ultrasound system for phase determination in echocardiography, the system comprising:
a wireless heart rate sensor for providing a pulse signal for a patient, the pulse signal indicating one heart beat without phasing per cardiac cycle;
an ultrasound echocardiography scanner configured to wirelessly receive the pulse signal, acquire an ultrasound image from a scan of the patient, and determine a phase for the ultrasound image to align with the pulse signal, wherein the ultrasound echocardiography scanner is configured to determine the phase for the ultrasound image from a heart cycle trace fit to the pulse signal; and
a display configured to display the ultrasound image and the phase.

14. An ultrasound system for phase determination in echocardiography, the system comprising:
a wireless heart rate sensor for providing a pulse signal for a patient, the pulse signal indicating one heart beat without phasing per cardiac cycle;
an ultrasound echocardiography scanner configured to wirelessly receive the pulse signal, acquire an ultrasound image from a scan of the patient, and determine a phase for the ultrasound image to align with the pulse signal; and
a display configured to display the ultrasound image and the phase, wherein the display is configured to display the phase as a percentage of the cardiac cycle or a marking on a simulated electrocardiography trace.

* * * * *